United States Patent [19]
Tiefenbrun et al.

[11] Patent Number: 5,425,765
[45] Date of Patent: Jun. 20, 1995

[54] SURGICAL BYPASS METHOD

[76] Inventors: Jonathan Tiefenbrun, 62 Country Rd., Mamaroneck, N.Y. 10543; Peter J. Wilk, 185 W. End Ave., New York, N.Y. 10023

[21] Appl. No.: 83,065
[22] Filed: Jun. 25, 1993
[51] Int. Cl.6 .................. A61F 2/04; A61F 2/06
[52] U.S. Cl. ............................. 623/12; 623/1; 623/66
[58] Field of Search ............. 623/1, 11, 12, 66; 606/151, 153, 155; 128/897, 898

[56] References Cited

U.S. PATENT DOCUMENTS

| | | | |
|---|---|---|---|
| 4,546,499 | 10/1985 | Possis et al. | 623/1 |
| 4,562,597 | 1/1986 | Possis et al. | 623/1 |
| 4,795,465 | 1/1989 | Marten | 623/12 X |
| 5,178,634 | 1/1993 | Ramos Martinez | 623/1 X |
| 5,197,976 | 3/1993 | Herweck et al. | 623/1 |
| 5,246,456 | 9/1993 | Wilkinson | 623/12 |
| 5,258,042 | 11/1993 | Mehta | 623/12 X |
| 5,275,622 | 1/1994 | Lazarus et al. | 623/1 |

FOREIGN PATENT DOCUMENTS 0173714 5/1992 U.S.S.R. ................. 606/151

Primary Examiner—David Isabella
Attorney, Agent, or Firm—R. Neil Sudol; Henry D. Coleman

[57] ABSTRACT

An endovascular bypass graft includes a tubular member, a first expandable mesh stent attached to one end of the tubular member, and a second expandable mesh stent attached to an opposite end of the tubular member. The second stent is provided with a plurality of fenestrations. The graft is inserted into a principal blood vessel such as the aorta and positioned in the vessel so that the fenestrations are aligned with junctions with ancillary blood vessels. The graft is attached to the principal blood vessel so that the fenestrations remain aligned with the respective junctions, thereby allowing blood flow between the principal vessel and the auxiliary vessels through the respective junctions upon completion of the bypass operation.

7 Claims, 1 Drawing Sheet

SURGICAL BYPASS METHOD

BACKGROUND OF THE INVENTION

This invention relates to a bypass graft. The bypass graft is useful for vascular bypass operations, for example, in bypass an aneurysm in the aorta. This invention also relates to a method for performing a bypass operation such as a vascular bypass operation.

Conventional endovascular operations to bypass an aortic aneurysm use a graft comprising a tubular member with wire lattices at opposite ends. The lattice at one end of the tubular member is inserted into the upstream end of the aorta and attached there, while two wire lattices at the opposite end of the tubular member are inserted into the upstream ends of the iliac arteries. A problem frequently arises in that there is not enough undamaged artery at the upstream end of the shunted section of the aorta to enable a successful attachment of the graft at the upstream end. More specifically, in many cases there is not enough undamaged aorta downstream of the junctions of the renal arteries and the superior mesenteric artery with the aorta.

OBJECTS OF THE INVENTION

An object of the present invention is to provide an improved graft for performing bypass operations.

Another object of the present invention is to provide an improved graft for vascular bypass operations.

A further object of the present invention is to provide an improved method for performing a bypass operation.

Yet another object of the present invention is to provide an improved method for performing a vascular bypass operation.

These and other objects of the present invention will be apparent from the drawings and detailed descriptions herein.

SUMMARY OF THE INVENTION

An endovascular bypass graft comprises, in accordance with the present invention, a tubular member, a first expandable mesh stent attached to one end of the tubular member, and a second expandable mesh stent attached to an opposite end of the tubular member. The second expandable mesh stent is provided with at least one fenestration alignable with a blood vessel junction upon an insertion of that stent into a principal blood vessel during a vascular bypass operation. The fenestration allows blood flow between the principal blood vessel and an auxiliary blood vessel through the junction upon completion of the bypass operation.

According to another feature of the present invention, the second expandable mesh stent is provided with a plurality of fenestrations in a predetermined relative configuration alignable with respective blood vessel junctions upon an insertion of the stent into the principal blood vessel during the vascular bypass operation.

The tubular member may be made of a fabric material such as Dacron. It is advantageous for the fenetrations to be elongated in an axial or longitudinal direction, as defined by the axis of the tubular member.

It is to be noted that the bypass graft can be used in bypass operations other than endovascular. Accordingly, a method for performing a bypass operation comprises, in accordance with the present invention, the steps of (a) providing a bypass graft comprising a tubular member provided with at least one fenestration, (b) inserting the graft into a hollow organ of a patient, (c) positioning the graft in the organ so that the fenestration is aligned with an internal organ junction, and (d) attaching the graft to the organ so that the fenestration remains aligned with the junction, thereby allowing communication between the hollow organ and an auxiliary organ through the junction upon completion of the bypass operation.

In accordance with another feature of the present invention, where the graft further comprises a pair of expandable mesh stents attached to opposite ends of the tubular member, one of the stents being provided with the fenestration, the step of attaching includes the step of securing the one of the stents to the hollow organ.

Where the hollow organ is an organ of the circulatory system and the auxiliary organ is a blood vessel such as the aorta, the method further comprises the steps of cutting the aorta longitudinally and laying open a wall of the aorta. The one stent is then inserted into an upstream segment of the aorta. Preferably, the one stent is provided with a plurality of fenestrations which are aligned with the renal arteries and the superior mesenteric artery.

An operation with a stent or graft in accordance with the present invention solves the problems of conventional aortic operations to bypass aneurysms. The cuff or stent at the upstream end of the tubular member can be inserted completely into a healthy segment of the aorta, without any danger of blocking communication with ancillary arteries, namely, the renal arteries, the superior mesenteric artery, and possibly the celiac axis.

DETAILED DESCRIPTION

Figure 1:
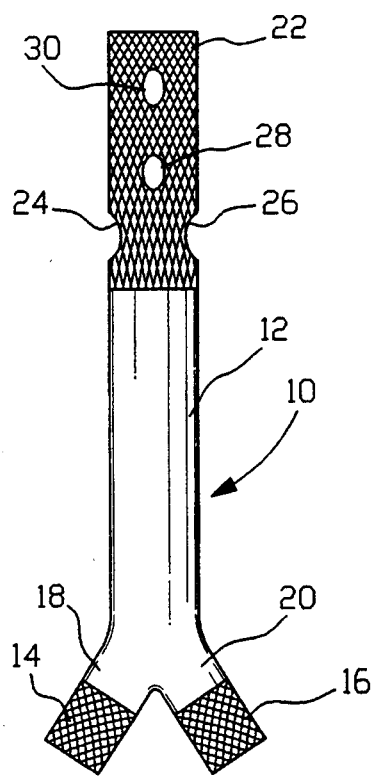
FIG. 1 is a schematic side elevational view, on a reduced scale, of an endovascular graft in accordance with the present invention.

As illustrated in FIG. 1, an endovascular bypass graft 10 comprises a tubular member 12, two expandable mesh stents 14 and 16 attached to respective graft branches 18 and 20 at one end of the tubular member, and another expandable mesh stent 22 attached to an opposite end of the tubular member. Stent 22 is provided in a sidewall with two substantially opposed fenestrations 24 and 26 alignable with renal arteries RA1 and RA2 (FIG. 2A) and two substantially longitudinally aligned fenestrations 28 and 30 respectively alignable with the superior mesenteric artery SMA and the celiac axis CA of a patient's aorta AO upon insertion of stent 22 into an upstream aortic segment UAS (FIGS. 2B and 2C) during an operation bypassing an aneurysm ASM in the aorta.

Graft 10 is installed in a patient's vascular system in a procedure essentially identical to conventional bypass operations except that, with the provision of fenestrations 24, 26, 28, and 30 in stent 22, the graft 10 must be manipulated during insertion to align the fenestrations with the respective junctions of aorta AO with tributary arteries RA1, RA2, SMA, and CA. To that end, fenestrations 24, 26, 28, and 30 are advantageously elongated in the longitudinal direction, as shown in FIG. 1.

Prior to an aortic bypass operation utilizing graft 10, the patient is subjected to a CAT scan to determine the exact angular locations and relative longitudinal positions of the vascular junctions of aorta AO with tributary arteries RA1, RA2, SMA, and CA. An appropriate aortic graft with fenestrations matching those of the patient is then selected from hospital inventory or ordered.

Fenestrations 24, 26, 28, and 30 are formed, for example, by bonding the lattice material of stent 22 to respective defining rings of an elastic biocompatible material.

Figure 2A:
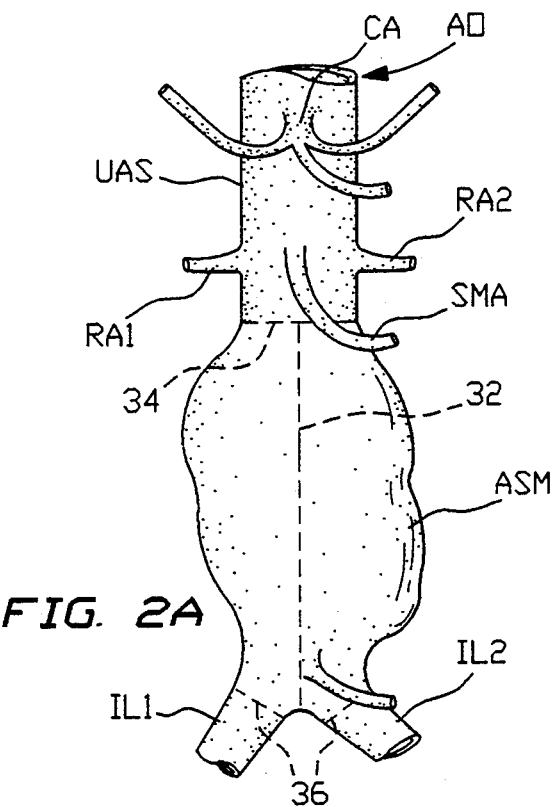
FIG. 2A–2C are schematic side elevational views of a portion of an aorta, showing successive steps in an aortic bypass operation using the graft of FIG. 1, in accordance with the present invention.

During an aortic bypass operation, as depicted in FIG. 2A, aorta AO is cut along a longitudinal line 32, a transverse upstream line 34, and a pair of substantially transverse downstream lines 36. Upstream line 34 is continguous with and substantially orthogonal to longitudinal line 32. Transverse line 34 is immediately downstream of superior mesenteric artery SMA and renal arteries RA1 and RA2, thereby leaving a cuff which is too small to adequately anchor an upstream side of a graft with a conventional continuous stent.

Figure 2B:
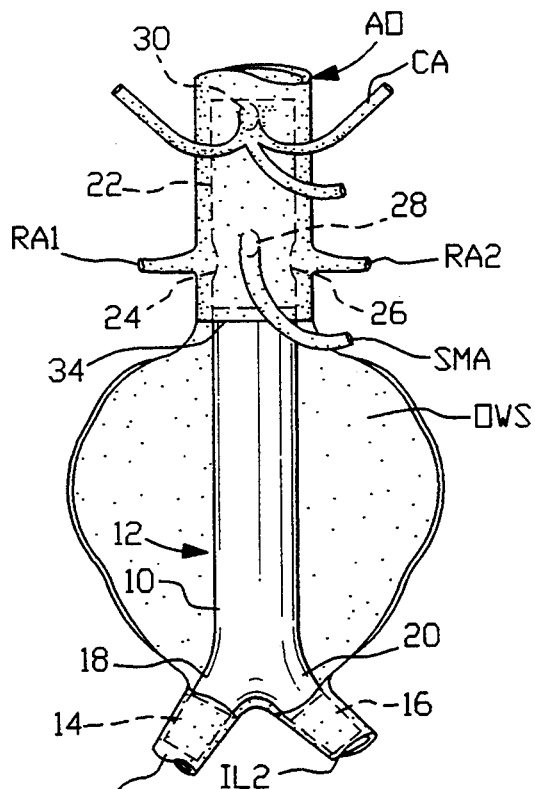
Figure 2C:
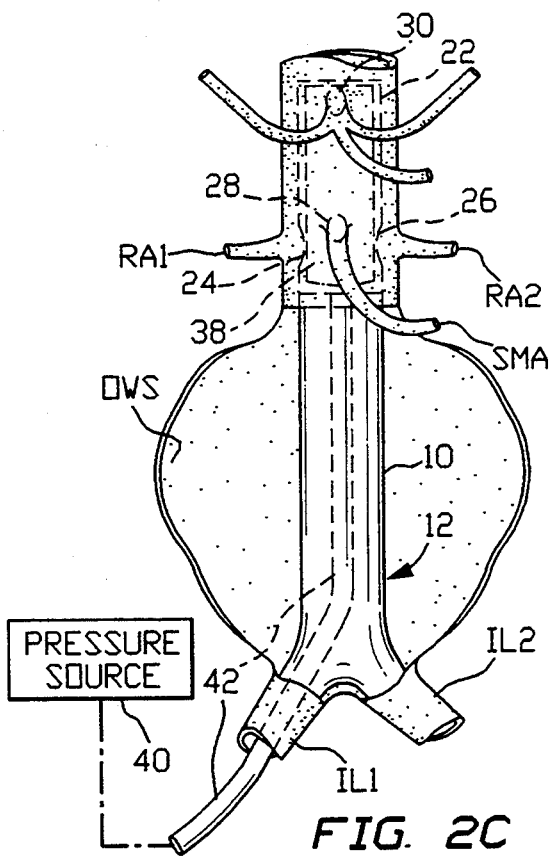

Upon the cutting of aorta AO along lines 32, 34 and 36, the aorta is laid open in the region of aneurysm ASM to form an opened wall segment OWS, as depicted in FIG. 2B, in a conventional bypass procedure. Stent 12 is then inserted into upstream aortic segment UAS so that fenestrations 24, 26, 28, and 30 are aligned with the junctions of tributary or auxiliary arteries RA1, RA2, SMA, and CA of aorta AO. Upon proper fenestration alignment, a balloon 38 (FIG. 2C) is inserted into stent 22 in a conventional step. Balloon 38 is connected to a pressure source 40 via a conduit 42, e.g., a catheter, and is quickly inflated to forcibly expand stent 22 into contact with the inner surface of upstream aortic segment UAS.

Upon the disposition of stent 22 in upstream aortic segment UAS such that fenestrations 24, 26, 28, and 30 are aligned with tributary or auxiliary arteries RA1, RA2, SMA, and CA, the fenestrations allow blood flow between the upstream segment of the aorta AO and auxiliary arteries RA1, RA2, SMA, and CA through the respective vascular junctions.

It is to be noted that graft 10 and the associated alignment of fenestrations 24, 26, 28, and 30 with tributary or auxiliary arteries RA1, RA2, SMA, and CA can be used in an otherwise known endovascular bypass procedure wherein the entire graft is inserted through an incision in a femoral (not shown) or one of two iliac arteries IL1 and IL2. The graft is subsequently guided through the selected iliac artery IL1 into aorta AO and positioned therein without the need for opening the aorta AO.

Although the invention has been described in terms of particular embodiments and applications, one of ordinary skill in the art, in light of this teaching, can generate additional embodiments and modifications without departing from the spirit of or exceeding the scope of the claimed invention. For example, the used of an expandable stent with fenestrations for alignment with internal organ junctions may be used in other kinds of bypass operations, such as coronary bypass operations, urinary bypass operations, gastrointestinal bypass operations, etc.

Accordingly, it is to be understood that the drawings and descriptions herein are profferred by way of example to facilitate comprehension of the invention and should not be construed to limit the scope thereof.

What is claimed is:

1. A method for performing a bypass operation, comprising the steps of:

providing a bypass graft comprising a tubular member having a sidewall provided with at least one fenestration;

inserting said graft into a hollow organ of a patient;

positioning said graft in said organ so that said fenestration is aligned with an internal organ junction; and attaching said graft to said organ so that said fenestration remains aligned with said junction, thereby allowing communication between said hollow organ and an auxiliary organ through said junction upon completion of said bypass operation.

2. The method defined in claim 1 wherein said graft further comprises a pair of expandable mesh stents attached to opposite ends of said tubular member, one of said stents being provided with said fenestration, said step of attaching including the step of securing said one of said stents to said hollow organ.

3. The method defined in claim 2 wherein said hollow organ is an organ of the circulatory system and said auxiliary organ is a blood vessel.

4. The method defined in claim 3 wherein said hollow organ is the aorta.

5. The method defined in claim 4 wherein said step of inserting includes the steps of cutting the aorta longitudinally and laying open a wall of said aorta, said one of said stents being inserted into an upstream segment of said aorta.

6. The method defined in claim 5 wherein said one of said stents is provided with a plurality of fenestrations, said step of positioning including the step of aligning said fenestrations with said renal arteries and said superior mesenteric artery.

7. The method defined in claim 2 wherein said step of securing includes the steps of inserting a balloon into said one of said stents and inflating said balloon to expand said one of said stents.

* * * * *